(12) United States Patent
Shih

(10) Patent No.: US 7,364,569 B2
(45) Date of Patent: Apr. 29, 2008

(54) RETRACTABLE SAFE SYRINGE

(76) Inventor: Chao-Hua Shih, 3F., No. 10, Wuchiuan 7th Rd., Wugu Shiang, Taipei (TW)

( * ) Notice: Subject to any disclaimer, the term of this patent is extended or adjusted under 35 U.S.C. 154(b) by 0 days.

(21) Appl. No.: 11/020,473

(22) Filed: Dec. 27, 2004

(65) Prior Publication Data
US 2005/0107747 A1    May 19, 2005

Related U.S. Application Data

(63) Continuation-in-part of application No. 10/747,053, filed on Dec. 30, 2003, now abandoned, which is a continuation-in-part of application No. 10/301,577, filed on Nov. 22, 2002, now abandoned.

(51) Int. Cl.
*A61M 5/00* (2006.01)
(52) U.S. Cl. .................... 604/187; 604/110
(58) Field of Classification Search ............ 604/187
See application file for complete search history.

(56) References Cited

U.S. PATENT DOCUMENTS

| 3,892,237 | A | * | 7/1975 | Steiner ............... 604/200 |
| 4,148,316 | A | * | 4/1979 | Xanthopoulos ......... 604/192 |
| 4,178,071 | A | * | 12/1979 | Asbell ................ 359/442 |
| 5,273,543 | A | * | 12/1993 | Bell et al. ............ 604/110 |
| 5,338,304 | A | * | 8/1994 | Adams ................. 604/110 |
| 5,693,023 | A | * | 12/1997 | Adams ................. 604/195 |
| 6,066,115 | A | * | 5/2000 | Chang Lai ............ 604/110 |
| 6,391,008 | B1 | * | 5/2002 | Tsai ................... 604/195 |
| 6,458,101 | B1 | * | 10/2002 | Hu ..................... 604/110 |
| 6,530,906 | B2 | * | 3/2003 | Hu ..................... 604/218 |
| 6,592,555 | B1 | * | 7/2003 | Wen-Pi et al. ......... 604/181 |
| 6,752,784 | B2 | * | 6/2004 | Tsai ................... 604/110 |
| 2003/0065290 | A1 | * | 4/2003 | Shyu .................. 604/187 |
| 2003/0199834 | A1 | * | 10/2003 | Hsu .................... 604/240 |

* cited by examiner

*Primary Examiner*—Nicholas D. Lucchesi
*Assistant Examiner*—Laura A. Bouchelle
(74) *Attorney, Agent, or Firm*—David I. Roche; Baker & McKenzie LLP

(57) ABSTRACT

A retractable safety syringe includes a needle set, a barrel and a plunger. The needle set is attached to the barrel, and has a first engaging portion at one end. The plunger is mounted with a compressive piston and terminates in a second engaging portion. The piston contacts with a shoulder of the barrel as the plunger is pushed forward. To withdraw the need set inside the barrel, the plunger is pushed forward while the piston contacts with the shoulder of the barrel so as to engage the first and second engaging portion. The plunger is thereby locked with the needle set for withdrawal inside the barrel.

18 Claims, 11 Drawing Sheets

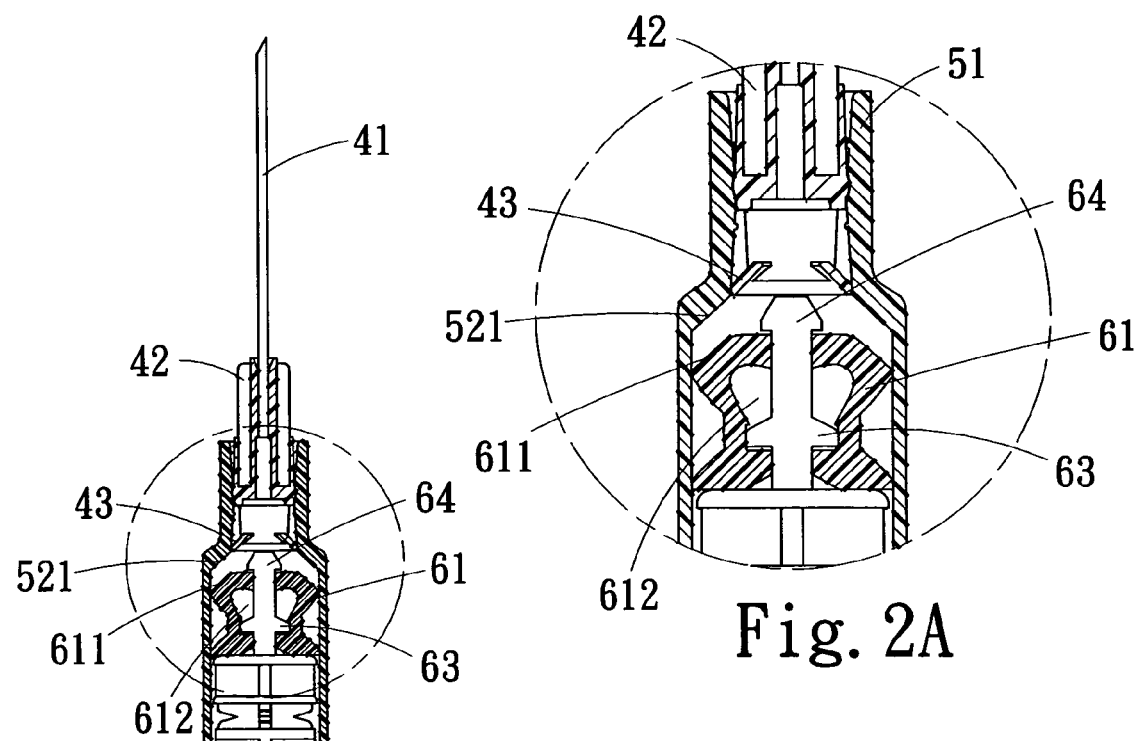
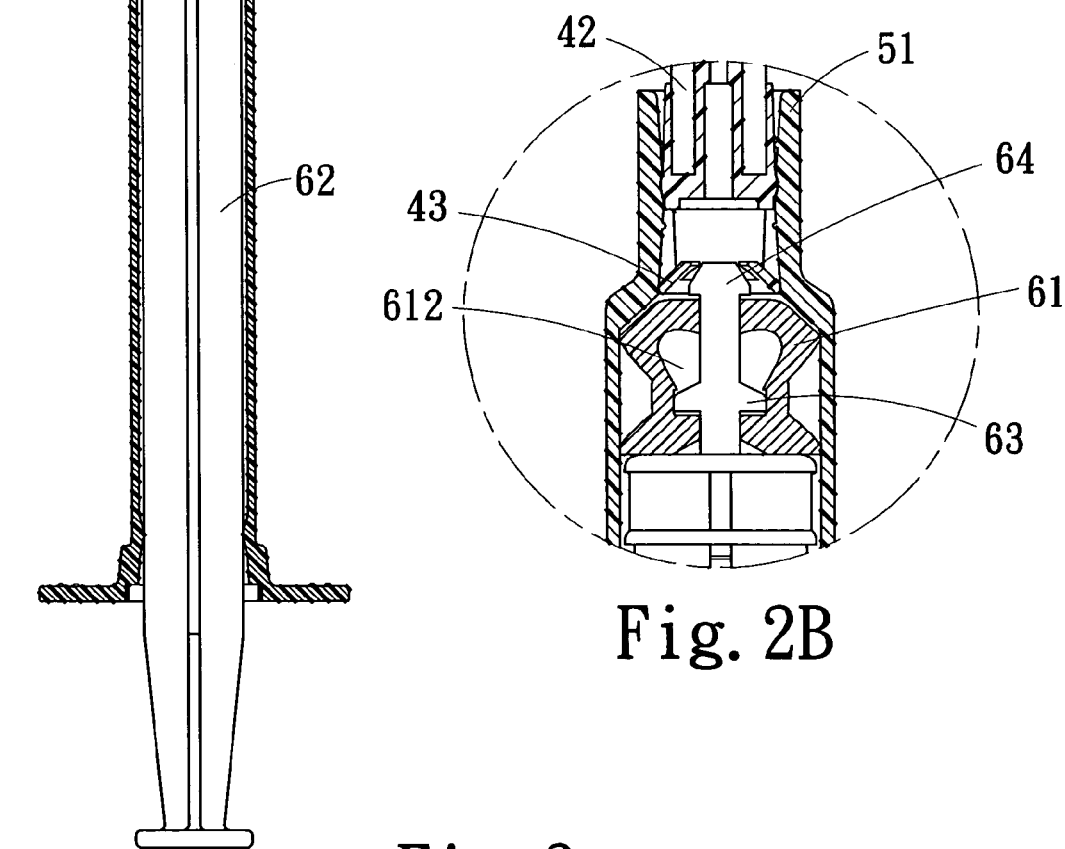
Fig. 2

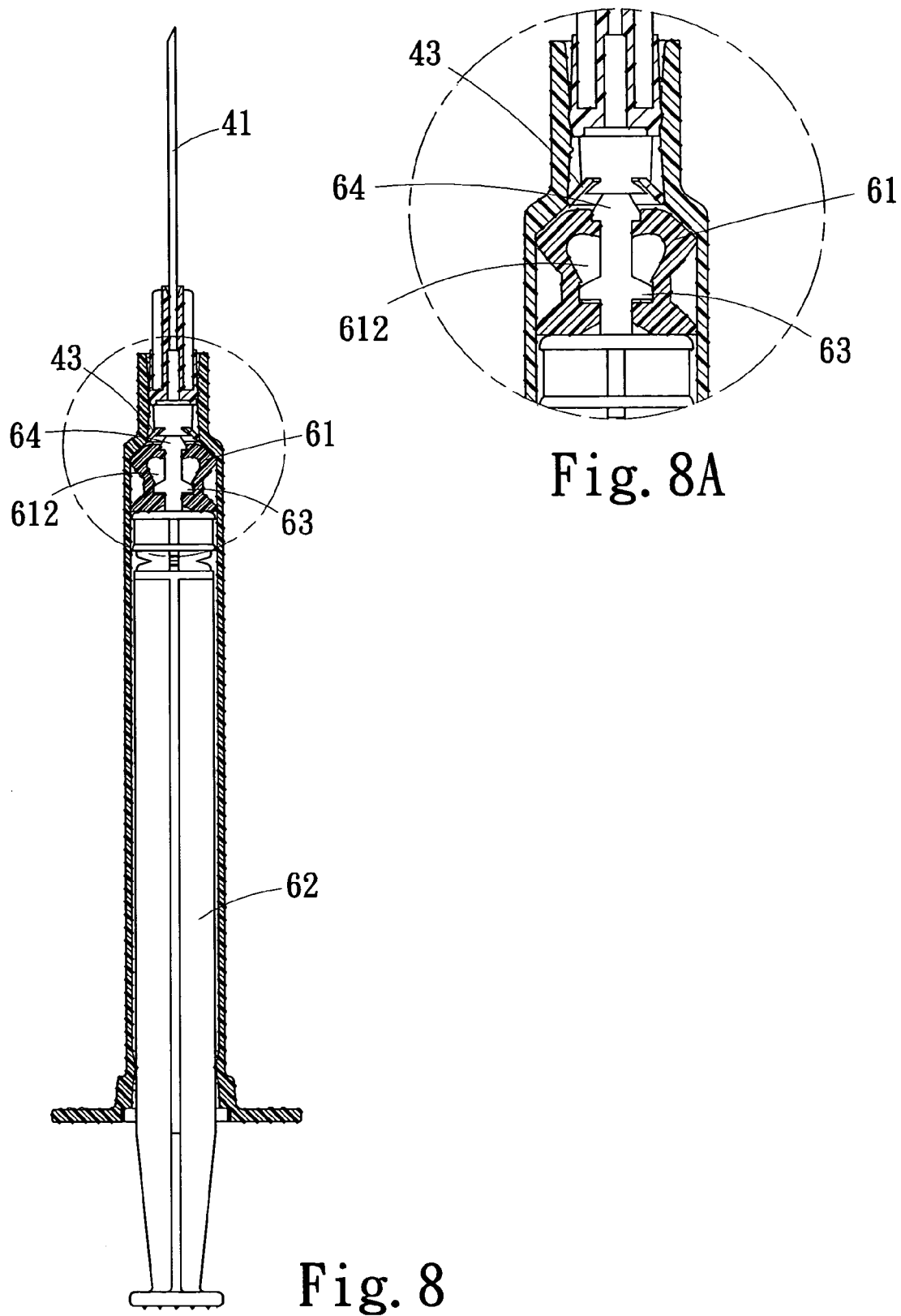

US 7,364,569 B2

RETRACTABLE SAFE SYRINGE

CROSS REFERENCE OF RELATED APPLICATION

This is a continuation-in-part application of the U.S. patent application having a Ser. No. 10/747,053 and a filing date of Dec. 30, 2003, now abandoned which is a continuation-in-part application of the U.S. patent application having a Ser. No. 10/301,577 and a filing date of Nov. 22, 2002 now abandoned.

BACKGROUND OF THE INVENTION

1. Field of the Invention

The present invention relates to a safety syringe having a needle retractable into a barrel, especially to a syringe having a piston which acts as a buffer to prevent inadvertent a locking engagement of the needle set.

2. Description of the Prior Art

One conventional type of syringes for subcutaneous injection is the disposable syringe which is discarded after a single use. The disposable syringe is convenient, hygienic and eliminates the risk of injection-related contaminations. However, one problem is that the discarded syringe has an exposed needle which may hurt a medical staff handling it. Even if the use of the conventional disposable syringe is safer with regard to the patient receiving the injection, risks of contamination and injuries still exist for the medical personnel, and more generally for the personnel in charge of treating the used syringes. Therefore, a retractable type syringe has been developed to retract the needle set inside the barrel after use.

A conventional retractable type safety syringe is shown in FIG. 11, wherein a barrel A terminates in a front end with a socket A1. The socket A1 can be used for fixing a needle set B, which includes a needle seat B1 having on a bottom formed with a first engaging portion B2. A plunger C having a pusher rod C1 and a piston C2 slides inside the barrel A. A top of the piston C2 is provided with a second engaging portion C3 engageable with the first engaging portion B2. A gap "d" defines a minimum distance between a top surface of the piston C2 and an opposite end surface of the barrel A without engagement between the first engaging portion B2 and the second engaging portion C3. Accordingly, a force is required to push the pusher rod C1 forwards in the last stage of injection to engage the first engaging portion B2 and the second engaging portion C3. After the plunger C and the needle set B are thereby locked each other, the pusher rod C1 is pulled backwards to retract the needle set B with its needle into the cylinder A. The syringe then can be discarded safely.

Safety syringes provided with spring retracting mechanisms and activating devices for automatically retracting needles are also known in the markets of medical appliances. In this type of device, a force is exerted on an activating device after injection, and the needle set will retract into the barrel by a spring retracting mechanism. Notwithstanding, a buffer gap between the front end of the pusher rod and the needle set is still used to define the disconnection between the pusher rod and the needle set before injection. This gap may result in a dosage error of a fluid to be drawn into the barrel. In addition, due to the resistance caused by the engagement of the first and second engaging portions, the user needs to exert a significant pushing force to discharge the liquid volume corresponding to the buffer gap during the injection operation, which may cause adverse injuries.

Therefore, there is presently a need for an improved retractable safety syringe provided with a mechanism that can ensure a dose of a fluid substance can be accurately drawn in the syringe, and prevent inadvertent locking engagement of the needle with the withdrawal mechanism.

SUMMARY OF THE INVENTION

A primary object of the present invention is to provide a retractable safety syringe having a buffer piston which can prevent inadvertent locking engagement of a needle set with a plunger.

A secondary object of the present invention is to provide a retractable safety syringe having a buffer piston which reaches its course end at a dosage volume reference of the barrel without locking engagement between a plunger and a needle set of the syringe. A user thereby can accurately control a dose of fluid substance drawn in the syringe and injected into a receiving body. The engagement of the needle set and the plunger can be operated after the syringe is taken out of the body of the patient, once all the dose of fluid substance has been discharged.

To achieve the above objectives, the retractable safety syringe of the present invention is comprised of a needle set, a barrel and a plunger. The needle set has a first engaging portion. An end of the barrel is formed with a needle-set socket. The needle set is connected to the needle-set socket. The plunger has a piston made of an elastic compressible material. In some embodiment, the piston may have a hollow space therein, and is in a shape easy to be compressed and restored. The plunger terminates with a second engaging portion, which may be arranged at the front end of the piston.

According to the present invention, the piston can be pushed inside the barrel till the top surface of the piston contacts a shoulder of the barrel without locking engagement between the first engaging portion and the second engaging portion. At the contact with the shoulder of the barrel, pushing further the plunger compresses the piston so that the projecting second engaging portion engages with the first engaging portion.

The present invention provides several kinds of embodiments of various shapes and structures of pistons. The piston can be configured so as to exert a force suitable for promoting the disconnection of the needle set from the barrel once the first and second engaging portions are connected each other. The present invention also provides other variant embodiments of the way the second engaging portion is arranged on the plunger.

The present invention will be apparent after reading the detailed description of the preferred embodiments in reference to the accompanying drawings.

BRIEF DESCRIPTION OF THE DRAWINGS

FIG. 2 is a schematic sectional view of the embodiment of FIG. 1.

FIG. 2A is a partially enlarged view of a mechanism for locking a needle set with a plunger according to the embodiment of FIG. 2;

FIG. 2B is a partially enlarged view of the locking mechanism of FIG. 2 in a state where a piston contacts with a shoulder of the barrel without locking engagement between the needle set and the plunger;

FIG. 8 is a schematic sectional view of another variation of a mechanism for locking a needle set with a plunger according to an embodiment of the retractable safety syringe of the present invention;

FIG. 8A is a partially enlarged view of the mechanism for locking a needle set with a plunger generally shown in FIG. 8;

DETAILED DESCRIPTION OF THE PREFERRED EMBODIMENT

Figure 1:
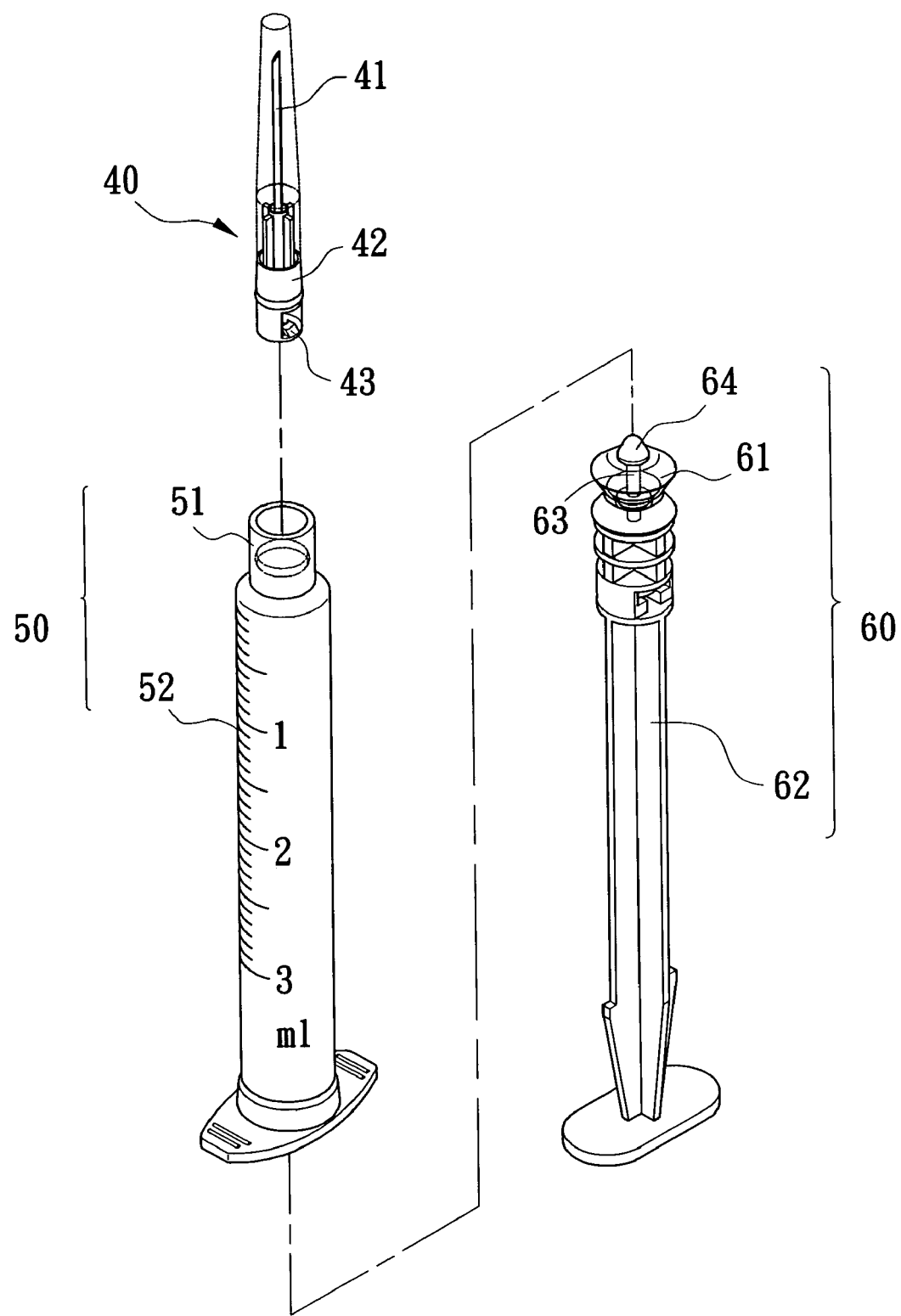
FIG. 1 is an exploded perspective view showing an embodiment of a retractable safety syringe of the present invention.

Referring to FIGS. 1, 2 and 2A, the retractable safety syringe of the present invention comprises: a needle set 40, a barrel 50 having a generally cylindrical shape, and a plunger 60. The needle set 40 at least includes a needle 41 and a needle seat 42 for fixing the needle 41. A bottom of the needle seat 42 has a first engaging portion 43 which is formed by at least a detent according to an exemplary embodiment of the invention. A lower end of the first engaging portion 43 connects with an inner bottom wall of the needle seat 42, and extends into a generally conical upper end which centrally forms a tapered opening. The first engaging portion 43 thus is centrally hollow communicating with the needle seat 42 and the needle 41 to form a passage for a fluid substance.

The plunger 60 is movable in translation along a hollow interior 52 of the barrel 50 to draw in or deplete a volume of fluid. The plunger 60 has a portion formed with a pusher rod 62, and axially extends into a piston shaft 63 on which is flexibly sleeved a piston 61. According to an embodiment, the piston 61 is made of an elastic material and defines an inner hollow space 612, and is in a shape that can be compressed and restored. The piston shaft 63 terminates with a second engaging portion 64 having a conical tip protruding out of the top surface 611 of the piston 61 in this embodiment. According to this embodiment, a portion of the engaging portion 64 may be in contact with the top surface 20 of the piston 61. The first engaging portion 43 and the second engaging portion 64 are engageable with each other to form a locking mechanism.

Figures 3, 3A:
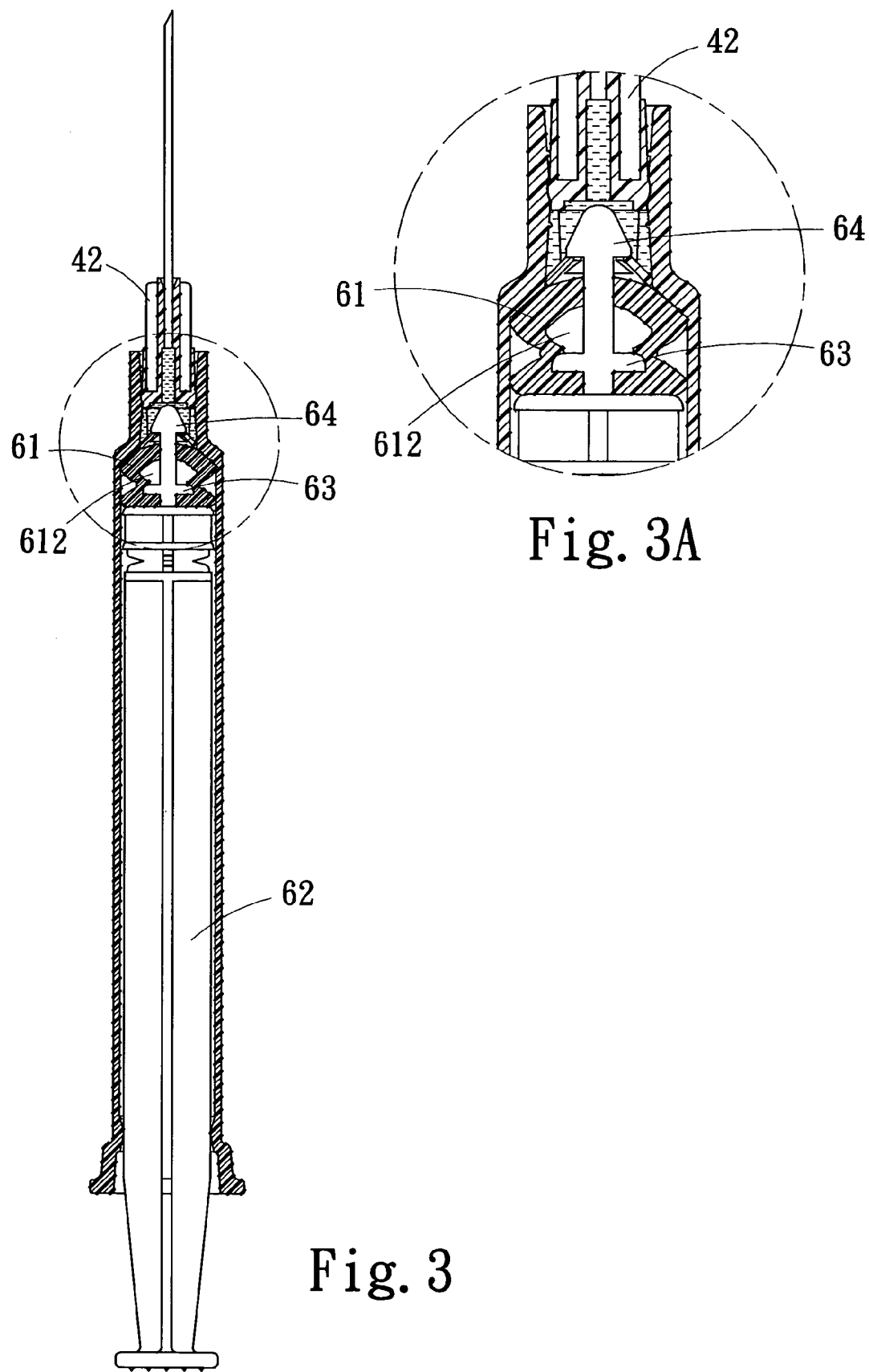
FIG. 3 is a schematic sectional view of the embodiment of FIG. 1 with the plunger being locked with the needle set according to an embodiment of the invention.
FIG. 3A is a partially enlarged view of FIG. 3 showing the locking engagement between the needle set and the plunger.
Figure 4:
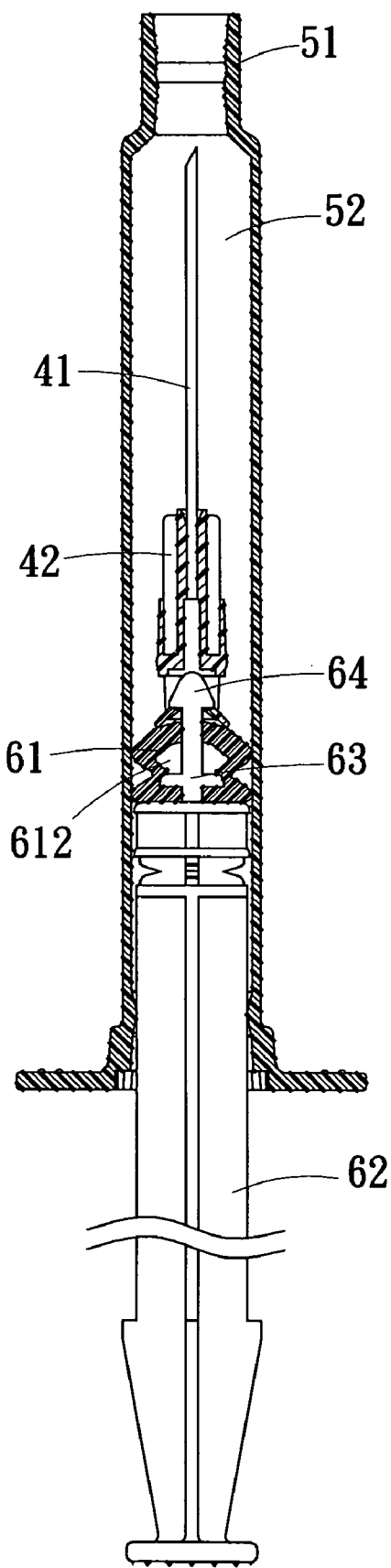
FIG. 4 is a schematic sectional view of the embodiment of FIG. 1 showing the needle set withdrawn within the barrel.

As shown in FIGS. 1, 2 and 2A, the piston 61 in this embodiment is composed of two conical elastic portions stacking one over the other, and having their round peripheries closely clung to the inner wall of the barrel 50. In operation for drawing in a liquid substance in the syringe, a doctor or a nurse pushes on the end of the pusher rod 62 to move the top surface 611 of the piston 61 to contact a shoulder 521 formed from an inner surface of the interior 52 of the barrel 50. When the top surface 611 of the piston 61 reaches the shoulder 521, the first engaging portion 43 is not yet connected with the second engaging portion 64 (referring to FIG. 2B). The user thus can draw a dose of a fluid substance in the syringe starting from a volume reference, which may be indicated as a "0" mark on the barrel. To inject the dose of substance confined in the syringe, the user inserts the needle 41 in the body receiving the injection, and pushes on the pusher rod 62 until the top surface 611 of the piston 61 contacts with the shoulder 521 in the interior 52 to fully discharge the dose of substance contained in barrel 50. When the top surface 611 of the piston 61 reaches the shoulder 521, the first engaging portion 43 is not yet connected with the second engaging portion 64. After completion of the injection, the user removes the syringe from the body receiving the injection. To ensure the used syringe is safely discarded, a user pushes further the pusher rod 62 while the top surface 611 of the piston 61 abuts against the shoulder 521, which presses and deforms the piston 61 to advance the piston shaft 63 and engage the first engaging portion 43 with the second engaging portion 64, as shown in FIGS. 3 and 3A. The plunger 60 thereby locks with the needle set 40 for withdrawal into the barrel 50. When the pushing force exerted on the pusher rod 62 is released, the restoring force of the piston 61 can help to overcome the connection force of the needle set 40 with a needle-set socket 51 of the barrel 50 as the user withdraws the needle set 40 into the cylinder 50 by pulling rearwards the pusher rod 62. The needle set 40 retracted into the barrel 50 thus will not be exposed out of the barrel 50, and the syringe can be safely 5 discarded.

Figures 5, 5A:
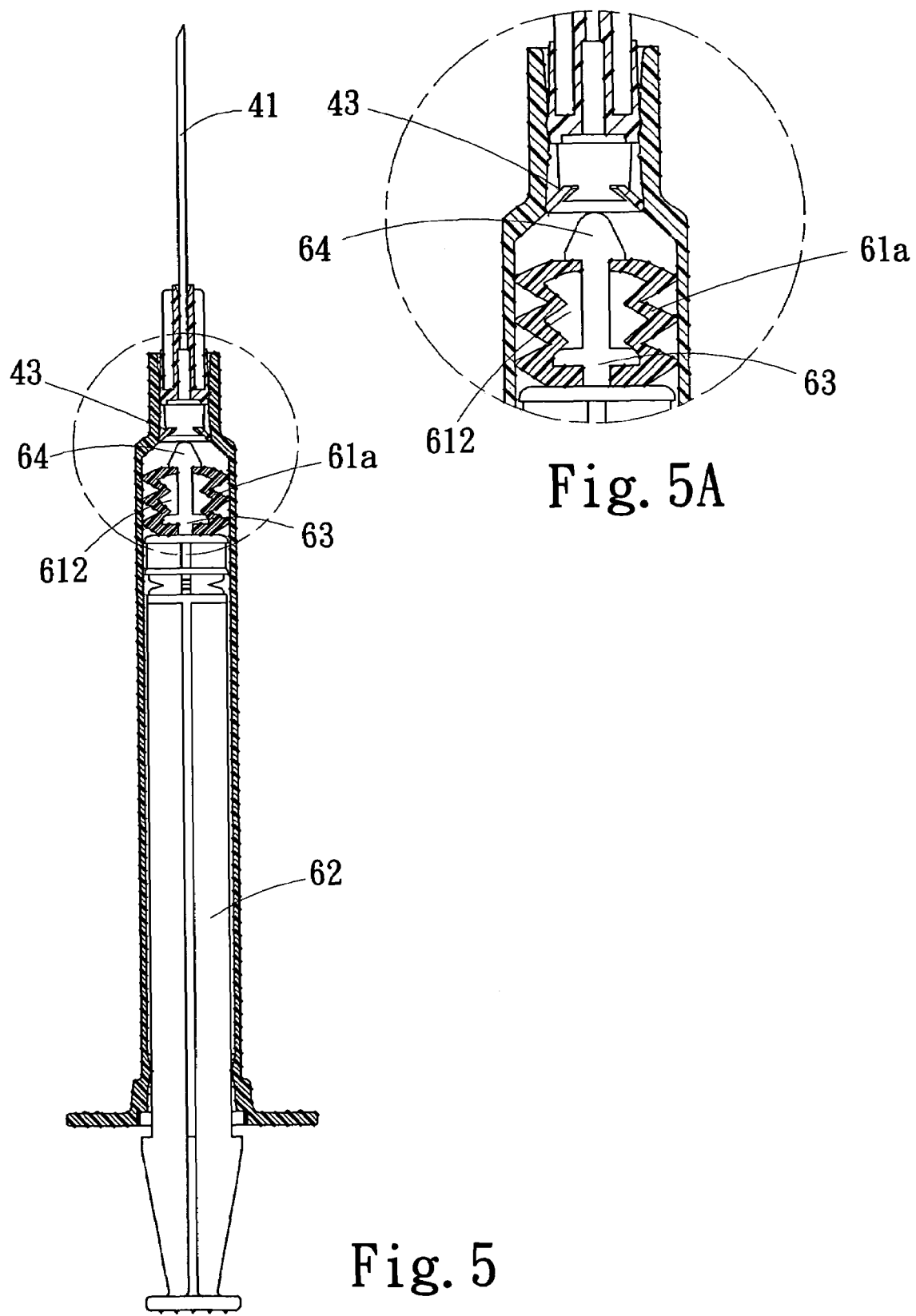
FIG. 5 is a schematic sectional view of another embodiment of the present invention.
FIG. 5A is a partially enlarged view of the embodiment of FIG. 5 showing a mechanism for locking the needle set with the plunger.
Figures 6, 6A:
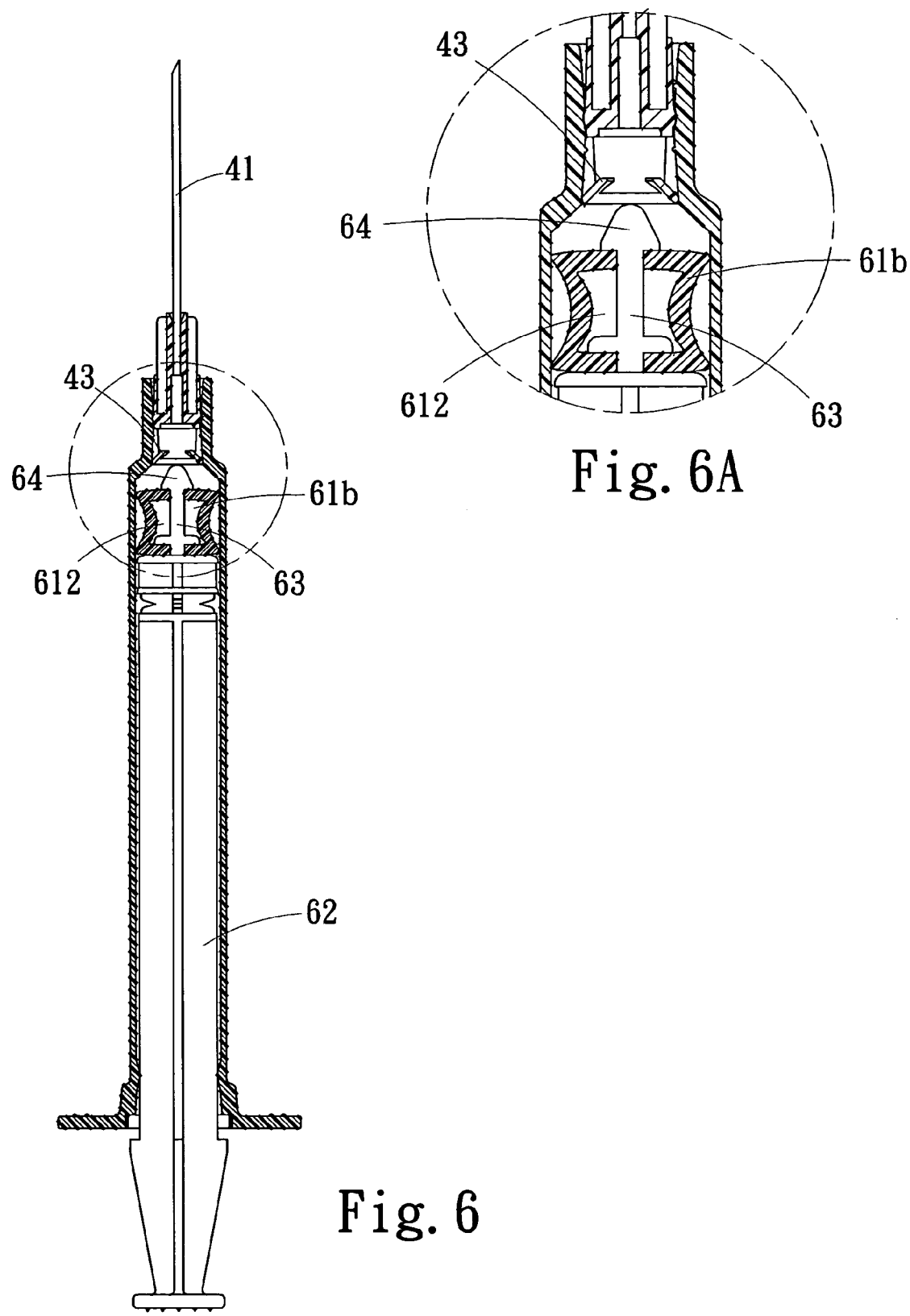
FIG. 6 is a schematic sectional view of another variant embodiment of the present invention.
FIG. 6A is a partially enlarged view of the embodiment of FIG. 6 showing a mechanism for locking the needle set with the plunger.
Figures 7, 7A:
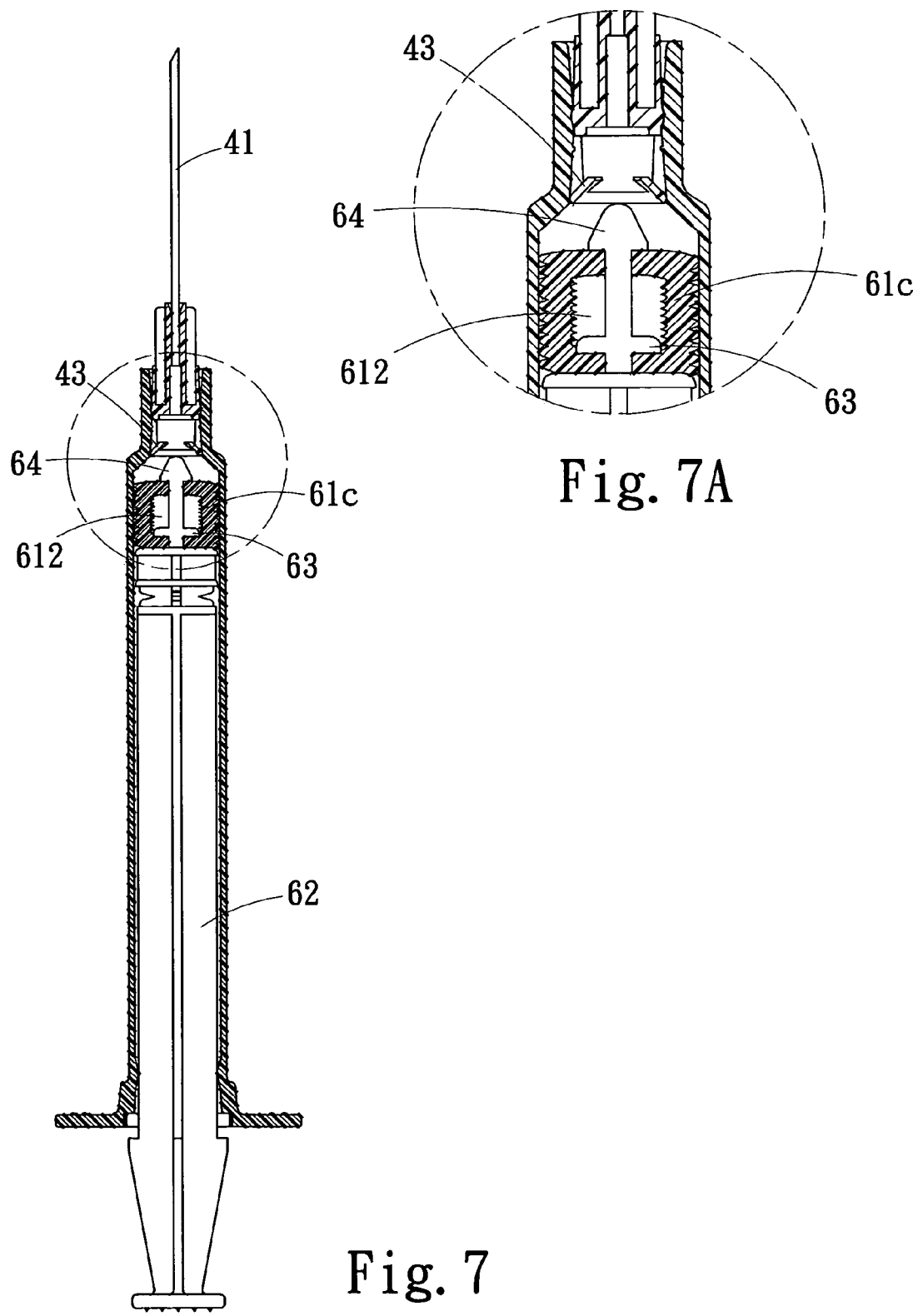
FIG. 7 is a schematic sectional view of another variation of the retractable safety syringe according to the present invention.
FIG. 7A is a partially enlarged view of the embodiment of FIG. 7 showing a mechanism for locking the needle set with the plunger.

Many variations of the foregoing embodiments can be envisaged within the scope of the invention. FIGS. 5 and 5A show another embodiment, in which the piston, illustrated with reference number 61a, has at least two round-disk shaped portions stacking on each other. FIGS. 6 and 6A show a variant embodiment in which the piston 61b includes a reduced middle neck portion. FIGS. 7 and 7A show another variation in which the piston 61c forms a post with a thread on its surface.

Figures 9, 9A:
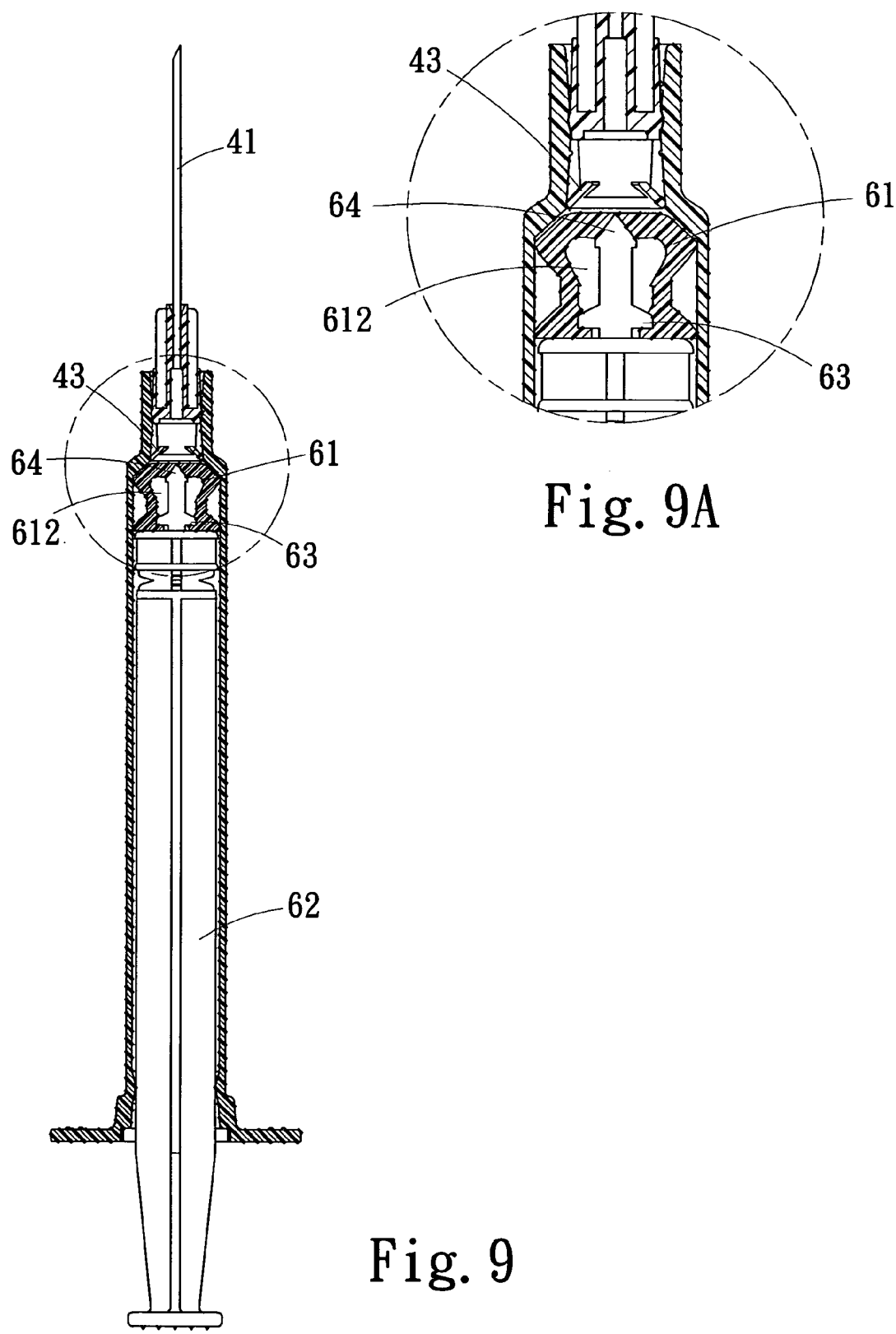
FIG. 9 is a schematic sectional view of another embodiment of the locking mechanism according to the present invention.
FIG. 9A is a partially enlarged view of the locking mechanism of FIG. 9.

Further, other embodiments may be envisaged with respect to the second engaging portion 64. In the foregoing illustration, the implementation of the second engaging portion is protruding out of the top surface 611 of the piston 61. Notwithstanding, the implementation can also be disposed at a different position relative to the top surface of the piston depending on the design or use requirements. FIG. 8 shows an embodiment in which a front portion of the engaging portion 64 protrudes out of the top surface 611 of the piston 61, while the remaining portions of the engaging portion 64 are positioned in the hollow space 612 of the piston 61. As shown in FIG. 9, the engaging portion 64 could be totally disposed within the piston 61 (i.e., the engaging portion 64 is totally covered by the piston 61). When a force is exerted to press and deform the piston 61, the engaging portion 64 protrudes out of the top surface 611 of the piston 61 to connect with the first engaging portion 43. Therefore, no matter the position of the engaging portion 64 is completely exposed to the outside of the piston 61 (as shown in FIG. 2), partially exposed to the outside of the piston 61 (as shown in. FIG. 8A) or completely received in the piston 61 (as shown in FIG. 9A), once a force is exerted to press and deform the piston 61, the engaging portion 64 extends out of the top surface 611 of the piston 61 to connect with the first engaging portion 43.

A person skilled in the art will appreciate that the first engaging portion and the second engaging portion can also be implemented with other mutually engageable shapes without departing from the scope of this invention.

Figures 10, 10A:
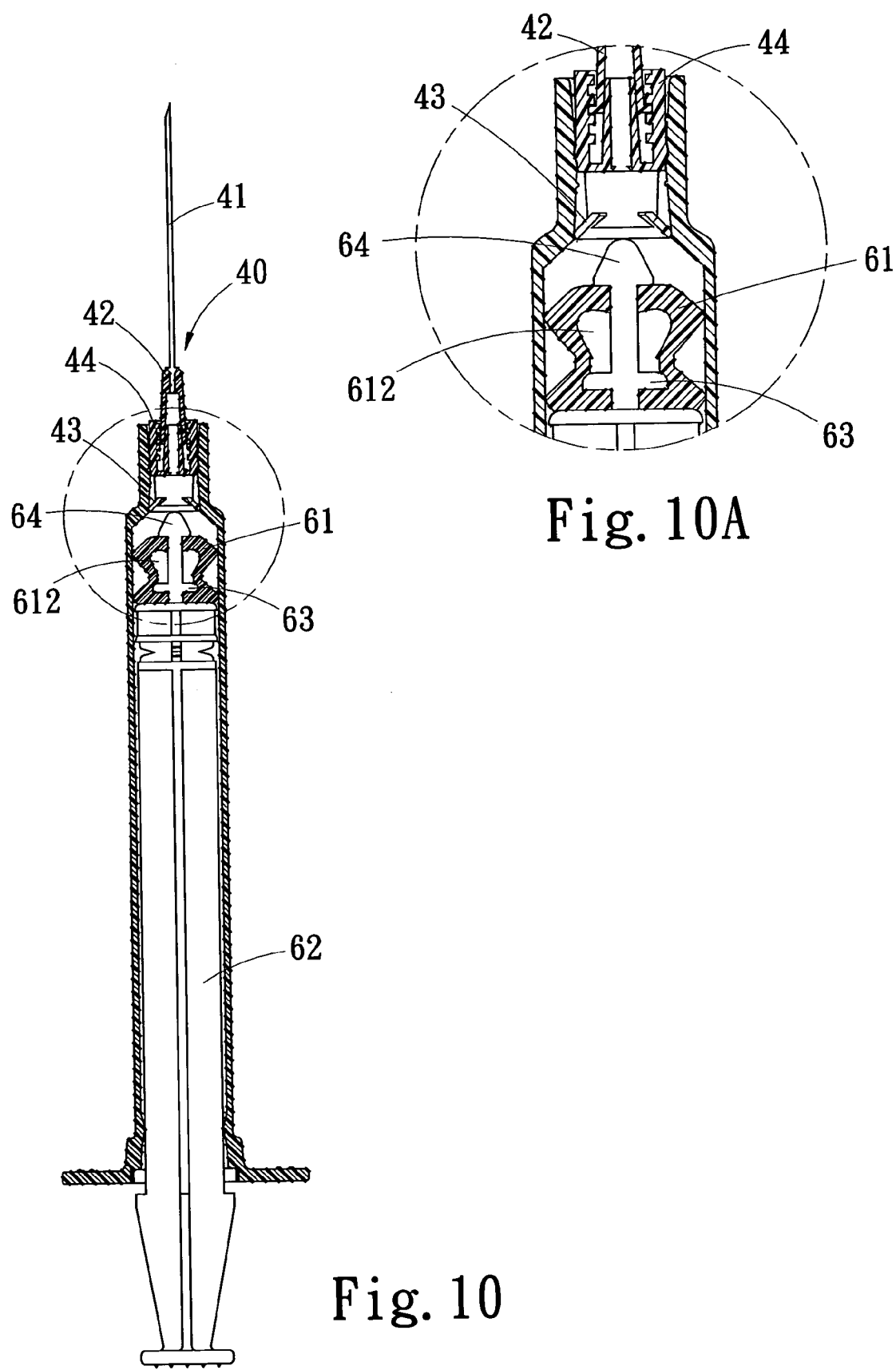
FIG. 10 is a schematic sectional view of a retractable safety syringe with an interchangeable needle according to an embodiment of the present invention.
FIG. 10A is a partially enlarged view of the locking mechanism generally shown in FIG. 10.
Figure 11:
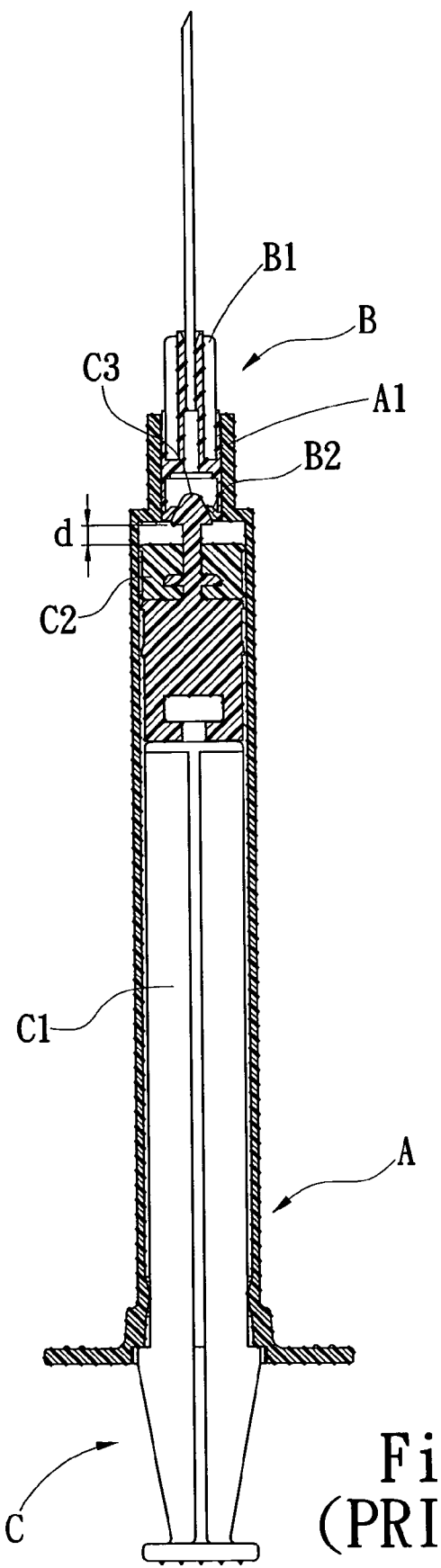
FIG. 11 is a schematic sectional view of a conventional retractable type safety syringe.

Again referring to FIG. 10, the needle set 40 of the present invention further can include an adapter 44. The adapter 44 is mounted at an end of the barrel 50, and is configured to detachably connect with the needle seat 42 carrying the needle 41. The detachable connection between the needle seat 42 and the adapter 44 can be, for example, a Luer-lock type connection effected by rotation, or a Luer-slip type connection by direct slipping engagement. In this embodiment, the first engaging portion 43 is formed at the bottom of the adapter 44. With the adapter 44, the needle 41 can thus be changed depending on the required use. FIG. 10 shows an example of rotatively connecting the needle seat. Other retractable syringes with different shapes and connecting modes of the needle seat are also possible with the present invention.

The structures disclosed herein can be used with various retractable safety syringes, and include at least the following advantages:

1. The restoring force of the piston under compression can help to overcome the connection force between the needle set and the needle-set socket, which may facilitate the retraction of the needle set into the barrel.
2. The syringe is configured with an initial volume reference which corresponds to an end of the injecting course of the piston of the plunger without locking engagement between the plunger and the needle set, which allows to accurately control the dose drawn in the syringe, and further ensures that it is fully expelled during the injection.
3. The piston acts as a buffer at its end course. The user has to exert an additional pushing force compressing the piston to connect the needle set with the plunger. Inadvertent locking engagement between the plunger and the needle set thus can be prevented.

As stated in the above disclosed, the present invention can surely attain its expected objects to provide a retractable safe syringe which is of simple structure, convenient for use and industrially valuable.

Having thus described my invention, what I claim as new and desire to be secured by Letters Patent of the United States are:

1. A retractable safety syringe comprising:
    a hollow barrel having a first end and a second end opposite the first end, wherein an inner surface of the barrel has an end wall with an opening that allows medication to exit the barrel;
    a needle set, including a needle and a needle seat for attaching the needle at the first end of the barrel, wherein the needle seat has a first connecting structure; and
    a plunger slidably mounted within the barrel, wherein one end of the plunger is mounted with a piston, and the plunger terminates with a second connecting structure engageable with the first connecting structure;
    wherein at one end of a translation course of the piston within the barrel, the piston contacts the end wall around to the opening, and further movement of the plunger towards the first end while the front surface of the piston is in contact with end wall of the barrel causes the first connecting structure to engage with the second connecting structure to lock the plunger with the needle set;
    wherein the translation course of the plunger is impeded by the contact between the piston and the end wall without engaging the first and second connecting structures.

2. The syringe according to claim 1, wherein the first and second connecting structures engage each other to lock the plunger with the needle set in a translation direction for withdrawal of the needle set inside the barrel.

3. The syringe according to claim 1, wherein the piston is made of a compressible material.

4. The syringe according to claim 1, wherein the first connecting structure includes a catching opening.

5. The syringe according to claim 4, wherein the second connecting structure includes a tapered tip end configured to snap fit through the catching opening.

6. The syringe according to claim 5, wherein the tip end is arranged outside the piston.

7. The syringe according to claim 5, wherein the tip end is configured to be receivable inside the piston.

8. The syringe according to claim 7, wherein the tip end is configured to protrude outward the piston as the plunger moves towards the first end to press the piston against the shoulder of the barrel.

9. A retractable safety syringe comprising:
    a hollow barrel having a volume reference adjacent to an end of the barrel; a needle set attached at the end of the barrel and provided with a first connecting structure; and
    a plunger movable along an interior of the barrel and including a piston and a second connecting structure engageable with the first connecting structure, wherein a distance between the piston and the volume reference defines a dose of fluid confined inside the barrel;
    the barrel having an end wall with an opening that allows medication to exit the barrel;
    wherein the dose of fluid confined inside the barrel is fully expelled when the piston comes into contact with the end wall of the barrel around opening, and further movement of the plunger towards the needle set while the piston remains in said contact causes the first connecting structure to engage with the second connecting structure to lock the plunger with the needle set;
    wherein the translation course of the plunger is impeded by the contact between the piston and the end wall without engaging the first and second connecting structures.

10. The syringe according to claim 9, wherein the first and second connecting structures engage each other to lock the plunger with the needle set in a translation direction for withdrawal of the needle set inside the barrel.

11. The syringe according to claim 9, wherein the volume reference includes a shoulder formed on an inner surface of the barrel adjacent to said end of said barrel.

12. The syringe according to claim 11, wherein the piston has a front surface abutting against the shoulder when the piston reaches the volume reference.

13. The syringe according to claim 9, wherein the piston is made of a compressible material.

14. The syringe according to claim 9, wherein the first connecting structure includes a catching opening.

15. The syringe according to claim 14, wherein the second connecting structure includes a tapered tip end configured to snap fit through the catching opening.

16. The syringe according to claim 15, wherein the tip end is arranged outside the piston.

17. The syringe according to claim 15, wherein the tip end is configured to be receivable inside the piston.

18. The syringe according to claim 17, wherein the tip end is configured to protrude outward the piston as the plunger moves towards the first end while the piston remains at the volume reference of the barrel.

* * * * *

UNITED STATES PATENT AND TRADEMARK OFFICE
CERTIFICATE OF CORRECTION

PATENT NO. : 7,364,569 B2  Page 1 of 1
APPLICATION NO. : 11/020473
DATED : April 29, 2008
INVENTOR(S) : Chao-Hua Shih It is certified that error appears in the above-identified patent and that said Letters Patent is hereby corrected as shown below:

On the Title Page, Item (73) Should Read,

The name of the Assignee is Life Shield Products, Inc., of Taipei, Taiwan, ROC

Signed and Sealed this

Twenty-fifth Day of November, 2008

JON W. DUDAS
*Director of the United States Patent and Trademark Office*